United States Patent [19]

Shapiro et al.

[11] 3,953,172

[45] Apr. 27, 1976

[54] METHOD AND APPARATUS FOR ASSAYING LIQUID MATERIALS

[75] Inventors: Stephen I. Shapiro, Scarsdale, N.Y.; Gerhard Ertingshausen, Cliffside Park, N.J.

[73] Assignee: Union Carbide Corporation, New York, N.Y.

[22] Filed: May 10, 1974

[21] Appl. No.: 468,649

[52] U.S. Cl. ............................ 23/230 R; 23/230 B; 23/230.3; 23/253 R; 23/259; 73/61.1 C; 233/26; 424/1

[51] Int. Cl.$^2$.................. G01N 33/16; G01N 31/08; G01N 23/12

[58] Field of Search .......... 23/230 R, 230 B, 253 R, 23/259; 233/26; 210/31 C, 198 C, 520, DIG. 23; 424/1; 73/61.1 C

[56] References Cited

UNITED STATES PATENTS

| | | | |
|---|---|---|---|
| 3,532,470 | 10/1970 | Rochte | 23/253 R |
| 3,555,284 | 1/1971 | Anderson | 23/259 |
| 3,586,484 | 6/1971 | Anderson | 23/259 X |
| 3,721,528 | 3/1973 | Mead et al. | 23/259 X |
| 3,759,666 | 9/1973 | Hill, Jr. | 23/259 X |
| 3,763,374 | 10/1973 | Tiffany et al. | 356/246 X |
| 3,798,459 | 3/1974 | Anderson et al. | 260/303 |
| 3,804,533 | 4/1974 | Scott | 356/246 |
| 3,829,223 | 8/1974 | Hamel | 23/259 X |

OTHER PUBLICATIONS

Grese et al., "Plasma Renin Concentration Measured by Use of Radioimmunoassay for Angiotensin I," Can. J. of Clin. Lab. Investig., Vol. 26 (4), Dec. 1970, pp. 334–367.

Ribi et al., "Chromatography of Microbial Lipids by Centrifugation Through Microparticulate Gel," J. of Bacteriology, Apr. 1970, pp. 250–260.

*Primary Examiner*—R. E. Serwin
*Attorney, Agent, or Firm*—Frederick J. McCarthy, Jr.

[57] ABSTRACT

Assaying of fluids to determine the level of a substance in a fluid sample such as blood serum involving the reacting of fluid samples with one or more reagents and centrifugally separating reaction constituents and measuring a property of a reaction constituents.

31 Claims, 10 Drawing Figures

METHOD AND APPARATUS FOR ASSAYING LIQUID MATERIALS

The present invention is directed to the assaying of fluids. More particularly, the present invention is directed to the determination of the level of a substance in a fluid sample, e.g. serum, by reacting a fluid sample with one or more reagents, and centrifugally separating reaction constituents to accurately obtain an indication of the level of the substance of interest.

In the analysis of fluids, e.g. serum, it is frequently important to determine in a fluid sample, the level of substances such as thyroid hormones, sex hormones, cardiac glycosides, vitamins, and cancer antigens. It is further extremely important that such levels be determined accurately and rapidly.

Previous techniques have involved time consuming, individual mixing, reaction, separation and measurement steps.

It is an object of the present invention to provide a method for rapidly and accurately assaying the level of substances in fluids.

Figure 1:
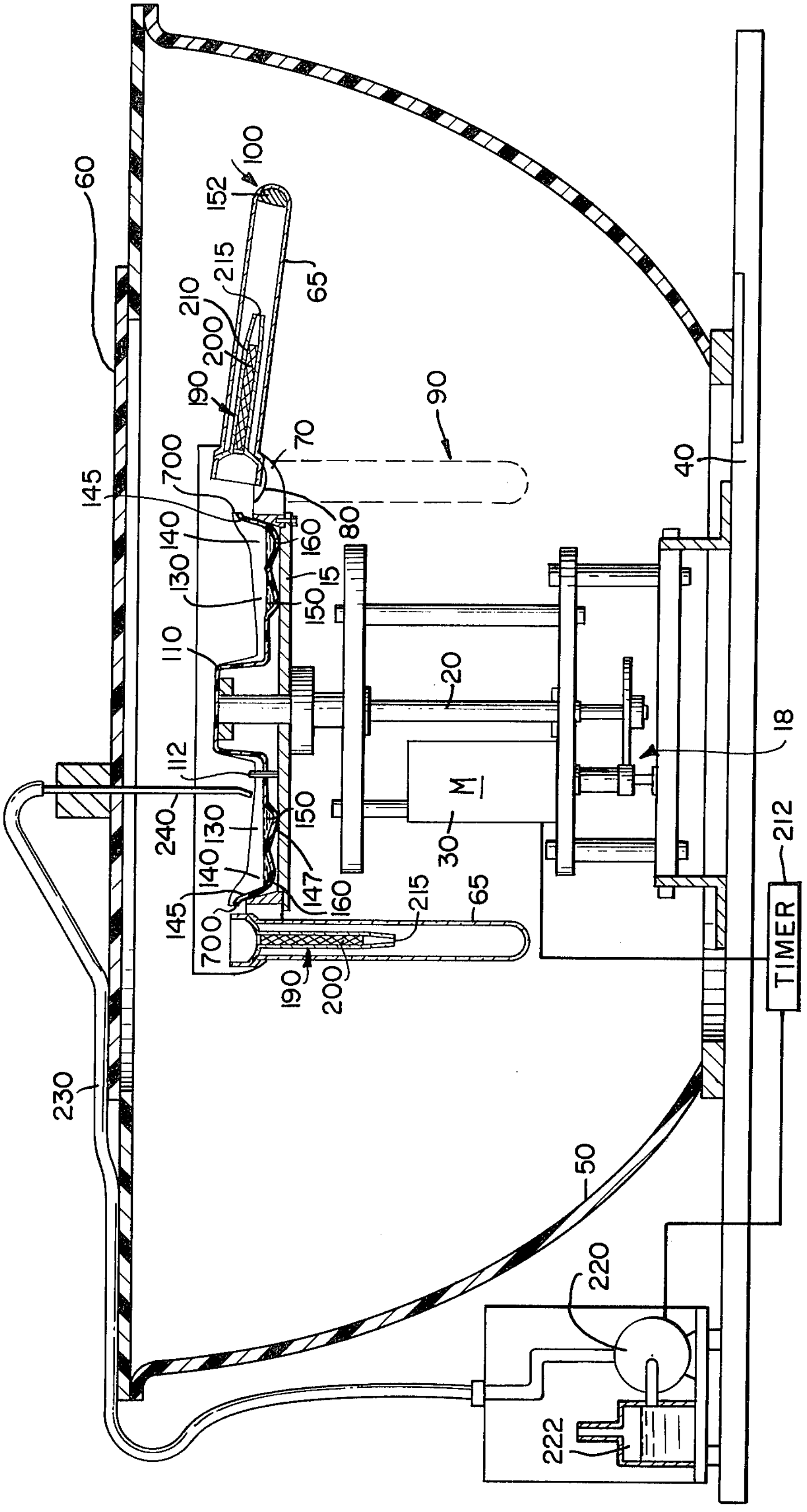
Figure 2:
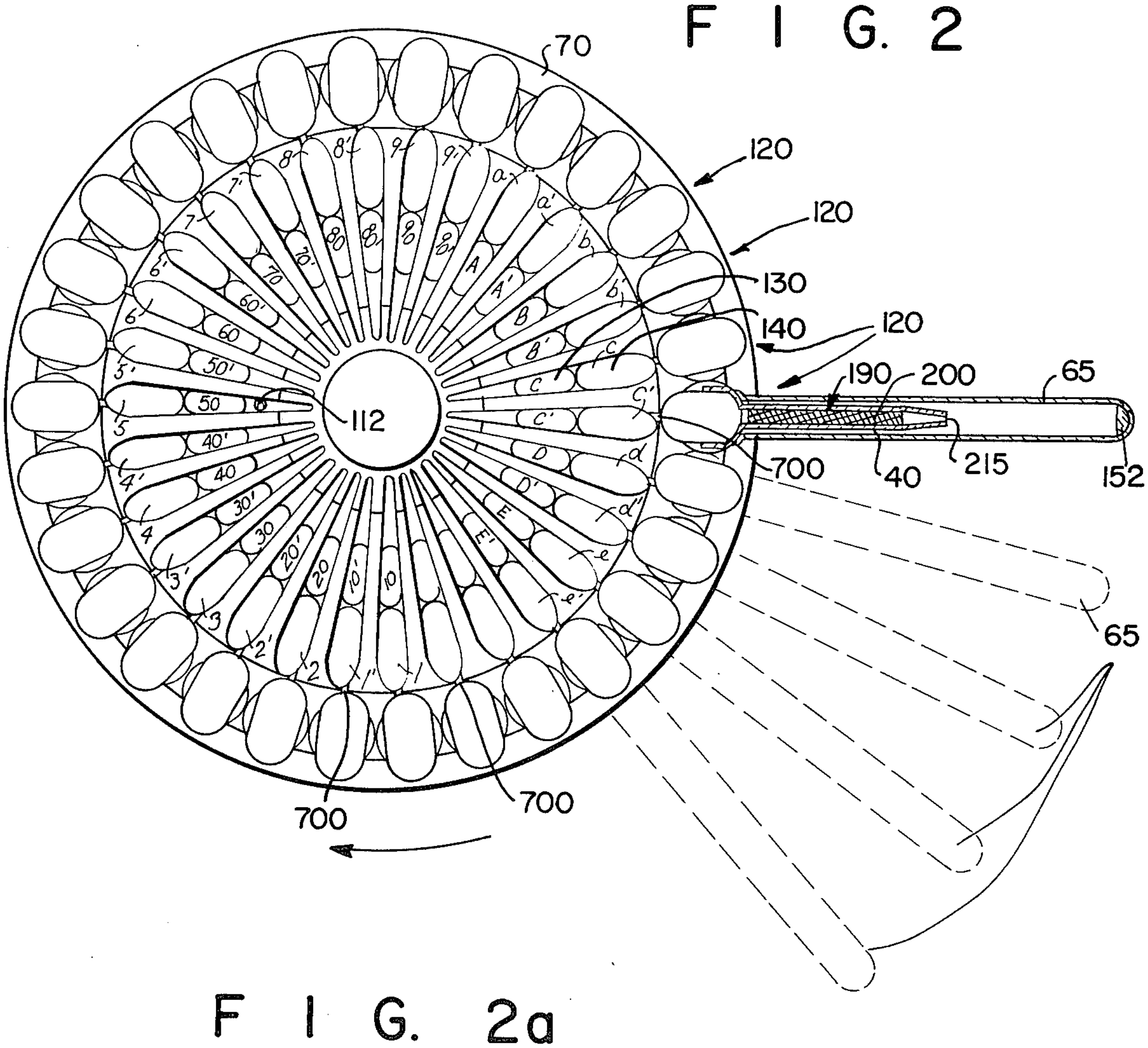
Figure 3:
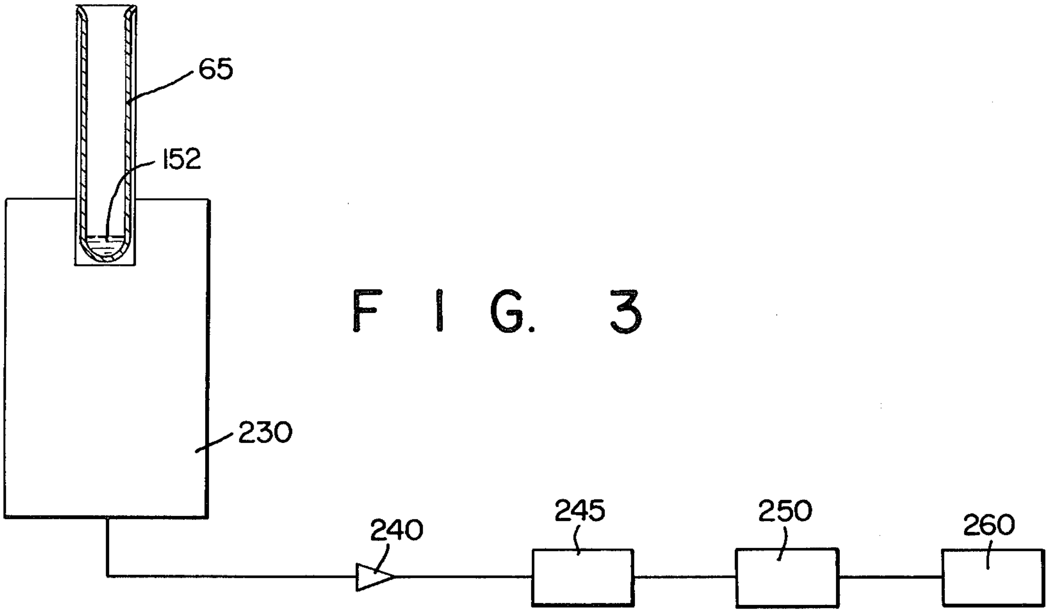
Figure 5A:
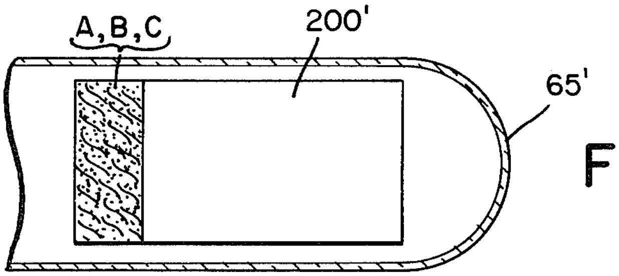
Figure 5B:
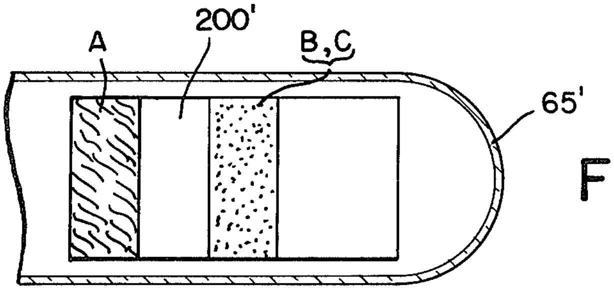
Figure 5C:
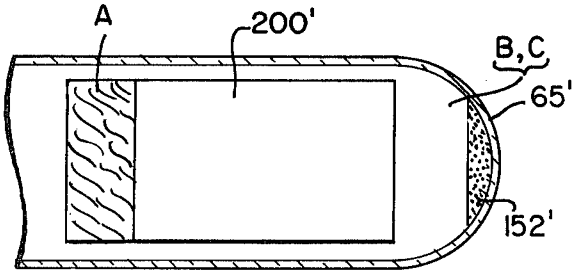
Figure 4:
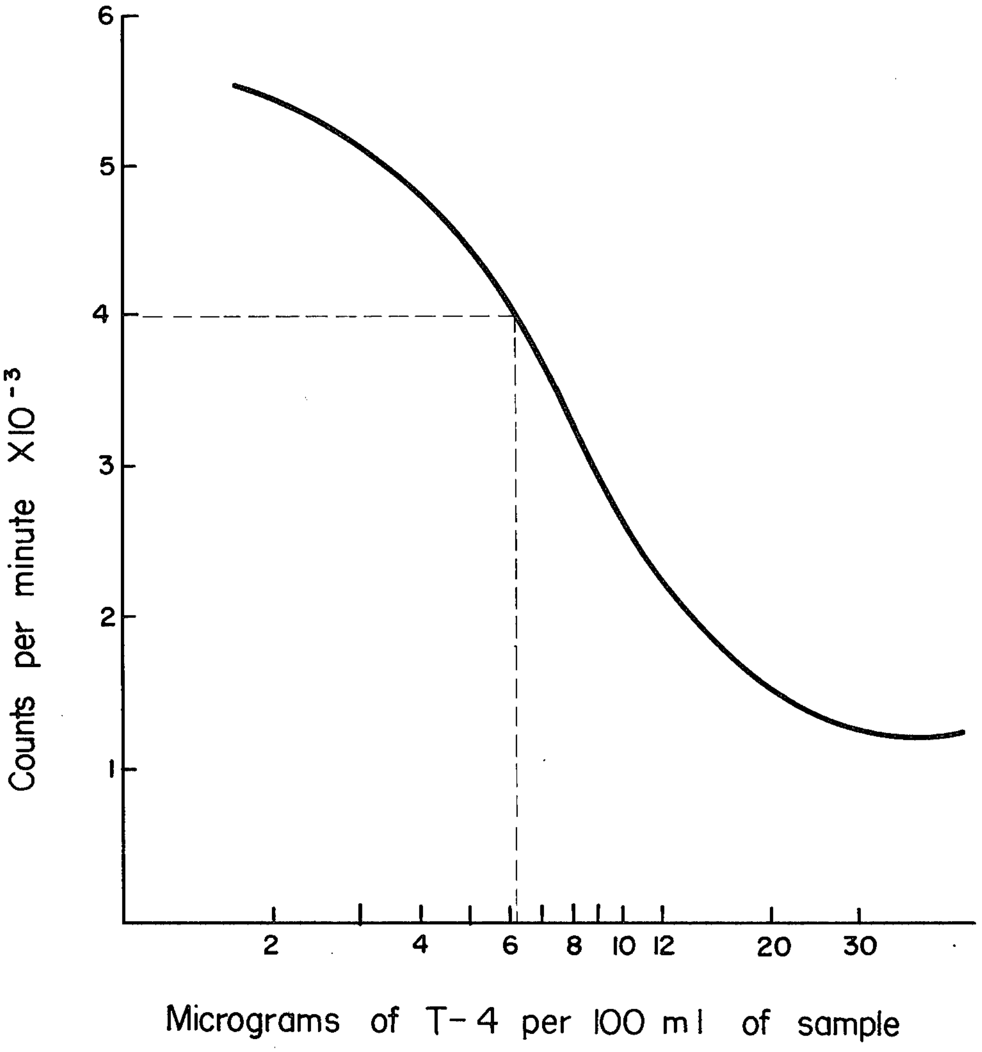
Figure 6:
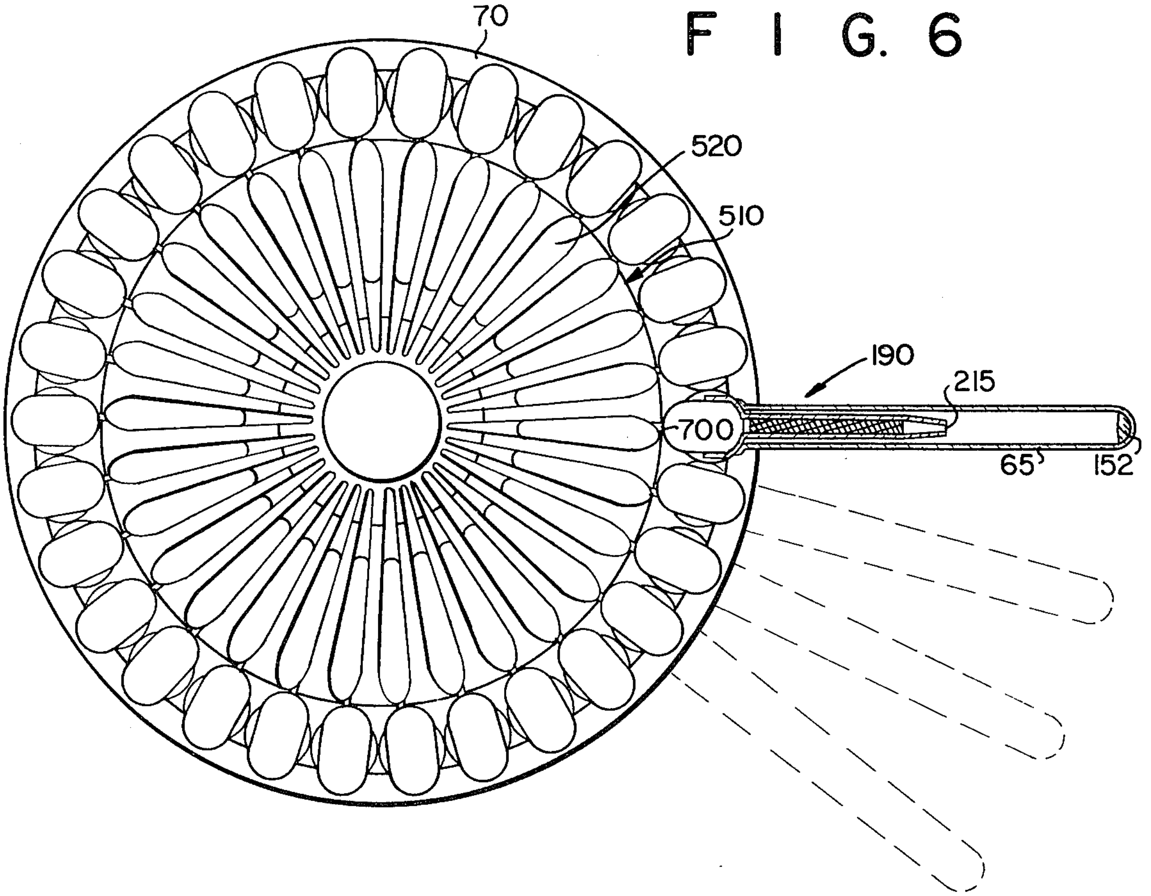
Figure 6A:
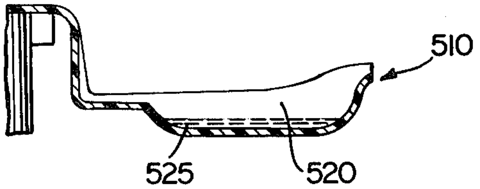

Other objects will be apparent from the following description and claims taken in conjunction with the drawing wherein FIG. 1 is an elevation view of an apparatus suitable for use in the practice of an embodiment of the present invention, FIG. 2 is a partial plan view of the apparatus of FIG. 1, FIG. 2(*a*) is a fragmented view of a portion of the apparatus shown in FIG. 2, FIG. 3 is a somewhat schematic representation of a measuring arrangement for use in accordance with the present invention, FIG. 4 is a representation of a graph of the type which can be used as a reference standard in accordance with the present invention, FIGS. 5(*a*), (*b*) and (*c*) illustrate schematically the functioning of liquid phase separating media in a particular embodiment of the present invention, and FIGS. 6 and 6(*a*) are a partial plan and elevation views of apparatus suitable for use in a further embodiment of the present invention.

A method in accordance with a particular embodiment of the present invention for assaying a plurality of liquid samples comprises (i) reacting at least two liquid materials in a plurality of cavities (ii) providing liquid phase separating means in communication with said cavities (iii) subjecting the cavities and liquid phase separating means to centrifugal force sufficient to transfer the liquid contents of the cavities to the communicating liquid phase separating means and to provide separation of the liquid transferred thereto into at least two phases and (iv) measuring at least one property of a separated phase.

The present invention will be more fully understood with reference to the drawing wherein FIG. 1 shows an apparatus suitable for use in the practice of the present invention comprising a rotatable support member 15 affixed to shaft 20 adapted to be driven by motor 30, which is coupled to shaft 20 as indicated at 18 over a range of speeds. The above-noted members are supported by base plate 40 and enclosed within housing 50 which is provided with a removable cover 60. Ring 70 is removably attached to rotating member 15 and supports a plurality of removable tubes 65 which are engaged with ring 70 by way of ball seat arrangements 80 such that the tubes are freely movable from rest position 90 to rotational position 100 upon suitable rotation of member 15. Disc 110 is removably mounted on member 15 and indexed thereon by means of pin 112 such that, with reference to FIG. 2, each row 120 of radially aligned cavities 130 and 140 are in susbstantial alignment with a tube 65. Tubes 65 are slightly displaced from exact radial alignment with opposite cavities 130 and 140 to compensate for inertia of liquid during transfer to tubes 65 and for a given apparatus can be routinely determined and adjusted.

By way of general description, in the practice of the present invention, for example for the purpose of obtaining the level of a substance in serum or serum-like samples, a precise amount of reagent 150 is placed in cavities 130 and a precise amount of serum 160 is placed in cavities 140, the reagent being such as to react with the substance in the sample, the level of which is sought, to produce a physically separatable reaction product. The cavities 130 and 140 can be thus loaded by manual pipetting or by use of the apparatus disclosed in U.S. Pat. No. 3,801,283 — S. Shapiro and T. Picunko issued Apr. 2, 1974. The motor 30 is accelerated to a first speed such that the centrifugal force developed causes reagent 150 from cavities 130 to be transferred to cavities 140 and mix with and interact with samples 160 in cavities 140. The speed of motor 30 is controlled such that the contents of cavities 140 are not forced out of cavities 140 by centrifugal force. Reagent 150 and samples 160 interact in cavities 140 and, with time, and an increasing amount of reaction product is formed in cavities 140 and ultimately an equilibrium condition would occur and after such time an analysis of the contents of cavities 140 could be used to determine by known techniques the level in samples 160 of the substance of interest. Such a practice would however be tedius at best and take an extended period of time, up to an hour or more for many applications. In the practice of the present invention, however, it is not necessary that the interaction in cavities 140 proceed to equilibrium, but only that a measurable amount of reaction product, or change in reactant amount be produced in cavities 140, whereupon the speed of motor 30 is increased to that at which the contents of cavities 140 are transferred by centrifugal force via channels 700 into liquid phase separation media devices 190 shown as chromatographic gel columns 200 contained in open topped glass envelopes 210 which are removably seated in tubes 65. The liquid material contacting the gel columns 200 is chromatographically separated thereby upon the application of eluent thereto. This is accomplished with the apparatus of FIG. 1 by dispensing a stream of a suitable liquid, e.g. buffer solution, from reservoir 222 via eluent pump 220 through conduit 230 and dispenser 240 into the cavities 130 promptly after the contents 160 of cavities 140 are transferred to gel columns 200. With reference to FIG. 1, pump 220 is actuated by way of a conventional timer arrangement 212 at a convenient time, e.g. 15 seconds, after the increased second speed is reached. Pump 220 provides a fixed flow rate of eluent for a fixed period of time and the total eluent quantity is automatically divided into the cavities 130. The eluent is transferred to gel columns 200 by centrifugal force via cavities 130 and 140. Upon transfer of eluent to gel columns 200, centrifugal force causes chromatographic separation of constituents of the liquid transferred from cavities 140. With appropriate selection of gel column 200, and with reference to the exemplary procedure hereinafter discussed, a reaction constituent in the material in the gel column can be rapidly separated by elution and transferred by centrifugal force via outlets 215 of envelope 210 to tubes 65 as shown at 152. In the instance where a reactant employed was radioactive, each tube 65 can be removed from ring 70 and the radioactivity of the contents 152 measured using the conventional arrangement of FIG. 3 comprising a gamma ray detector 230, e.g. a sodium iodide crystal/photomultiplier tube combination, amplifier 240, pulse height analyzer 245, counter 250 and a display device 260, e.g. a digital printer. The count thus obtained for each tube 65 can be related to the level in the sample of the substance of interest by computation or by comparison with a standard.

Figure 2A:
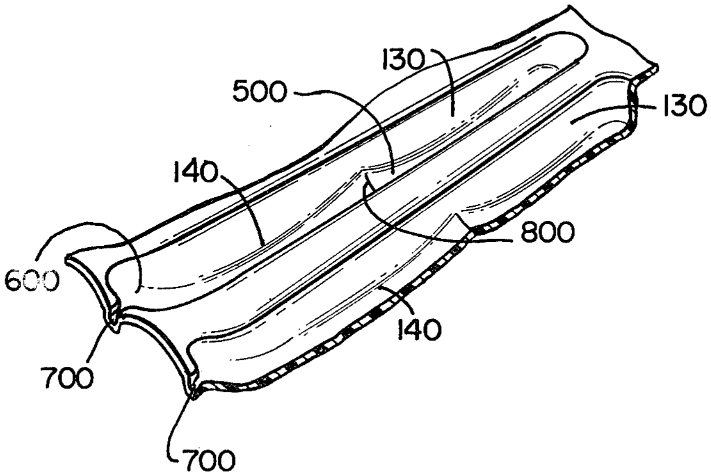

As shown in the particular embodiment of FIG. 2(*a*) a cavity 130 of the inner row communicates with the cavity 140 of the outer row with which is aligned by way of a trough-like passage means indicated at 500 which is formed by the side surfaces and rising bottom surface of an inner cavity 130. With sufficient rotation and centrifugal force, liquid in a cavity 130 is overflows raised portion 800 into an aligned outer cavity 140. Also, a cavity 140 of the outer row communicates with a liquid phase separation means 190 (not shown in FIG. 2*a*) which is aligned therewith by way of an extended trough-like means indicated at 600 which is formed by the side surfaces and rising bottom surface of an outer cavity 140, and channel 700. With sufficient rotation and centrifugal force liquid in an outer cavity 140 is overflowed and transferred into an aligned separating means. However, the slope 145 of outer cavities 140 is steeper than the slopes 147 of inner cavities 130, as shown in FIG. 1, so that liquid will be confined in the outer cavity 140, raised portion 600 forming a dam-like barrier, until an increased centrifugal force is applied which is greater than the centrifugal force required to overflow liquid from an inner cavity 130 to an outer cavity 140.

In the practice of the present invention, as above described, it is theoretically possible, for a given reaction and for given particular concentrations of reactants, to calculate the concentration of a reaction product, or reactant, at any given time after the start of the reaction, and a plot of concentration vs time obtained, with respect to which measured concentrations at particular times can be compared. For a simple case the procedure can be as follows:

For a hypothetical, bimolecular, irreversible reaction $A + B \rightarrow C$, where equal concentrations of A and B are mixed at time $t$=0, and at $t$=0, the concentration of C=0, it can be shown that the concentration at any time after $t$=) is given by:

$$C = \frac{A_o^2 K_1 t}{1 + a_o K_1 t}$$

Where:

Ao is the starting concentration of reactants A and B.

$K_1$=A (−Ea/RT) — Arrhenius Equation where A is the frequency factor, E*a* is the activation energy of the reaction, T is the temperature of the reaction and R is the universal gas constant.

With such a calculation, and a plot derived thereform, for the given reaction, the concentration measured after a relatively short reaction time, could be routinely converted into the total concentration or level of the substance of interest.

In a particular embodiment of the present invention, a standard is used which avoids the inconvenience of the above described approach. In this embodiment, with reference to FIGS. 1 and 2, a general procedure illustrative of this embodiment is to place antibody, as a reactant, in innermost cavities 130 of the disc 110, and serum samples containing an unknown amount of a substance, e.g. thyroxine (T-4), together with radioactive T-4 reagent and a displacement reagent, are placed in the outer cavities 140. The disc is rapidly accelerated to a first rotational speed in the course of which antibody reactant from the inner cavities 130 is caused to move by centrifugal force to the outer cavities 140 wherein the antibody and T-4 mix and react. In the course of the reaction, T-4 in the serum samples is displaced from its carrier and is free to compete with the radiolabeled T-4 for a limited number of binding sites on the antibody reactant. At any time after mixing and during the ongoing reaction in cavities 140, the ratio of the antibody-bound radiolabeled T-4, to the free radiolabeled T-4 in cavities 140 provides a measure of the initial level of T-4 in the serum samples. Thus, when the reaction has proceeded at the initial speed for a short time sufficient to provide meaningful radioactive counting data and well before reaction equilibrium is reached, the rotation of disc 110 is increased to a higher value at which contents of outer cavities 140 are thrown by centrifugal force into communicating separating media 200 wherein the T-4 antibody complex (containing both radioactive and non-radioactive T-4) is passed, together with unreacted antibody through the separating media 200 with the uncomplexed T-4 (both radioactive and non-radioactive) being adsorbed by the separating media 200.

This action halts the complexing reaction by removing at least one reactant (antibody) from the reaction environment (gel columns 200) and consequently a count of the radioactivity of the separated antibody T-4 complex, when compared to a standard, provides a measure of the initial T-4 content of the sample under test. The standard can be provided by using serum or serum-like materials of known but different T-4 levels and, using the same reaction conditions, as for the test samples above, plotting the radioactive counts (or ratio of counts) obtained for each material vs its known level of T-4. In a preferred practice, the "standard" materials are placed in appropriate cavities 140 in the same disc 110 used for the test samples of unknown T-4 level and the standard data and test data, are obtained concurrently.

FIG. 4, which is directly related to the specific example presented hereinbelow, illustrates a standard graph obtainable for use in the foregoing manner and shows the radioactive counts per minute obtained using standard starting materials containing a known amount of T-4. By way of example, FIG. 4 indicates, for the particular conditions employed, that when a count of 4,000 is obtained from a test serum sample run concurrently with the standard materials, the initial level of T-4 in a serum sample is 6.2 $\mu$ grams of T-4 per 100 ml of sample. It is, of course, understood that in practicing the present invention, appropriate and precisely controlled amounts of reactants are employed and the present invention is generally applicable to all liquid —liquid reactions, particularly those employed in the well-known clinical assaying techniques for blood serum or serum like materials using reagents known to the art.

The method of the present invention is particularly applicable to the assaying of a wide range of physiologically important molecules for example as disclosed in Clinical Chemistry Vol. 19, No. 2, 1973 (Article by D. S. Kelley, L. P. Brown and P. K. Besch at page 146).

The following example will further illustrate the present invention.

EXAMPLE

Clinical serum samples were analyzed to determine the level of thyroxine (T-4) therein using apparatus of the type illustrated in FIG. 1, 2 and 3 and a standard curve as shown in FIG. 4. Nine clinical serum samples of unknown T-4 level, in duplicate, and five standard solutions each of different, but known T-4 levels, in duplicate, were processed simultaneously. This was accomplished by loading two outer cavities 140 of disc 110 with 35 microliters each of a particular clinical serum sample, thus loading eighteen outer cavities in conveniently designated 1, 1'; 2, 2'; 3, 3'; — 9, 9' in FIG. 2. Also, two outer cavities 140 of disc 110 were loaded with 35 microliters each of a particular one of five standard solutions thus loading 10 outer cavities 140 conveniently designated *a, a'*; *b, b'*; — *e, e'* in FIG. 2. The T-4 levels in the standard solutions prepared as hereinbelow described, were as follows:

| Standard | T-4 (μgm/100ml) |
|---|---|
| a | 0 |
| b | 2 |
| c | 6 |
| d | 12 |
| e | 30 |

In the course of loading of the outer cavities as described above each 35 microliter quantity was mixed with 65 microliters of distilled water. Additionally, to each of the outer cavities 140 loaded as above described 50 microliters of a radioactive T-4-$^{125}$I solution (prepared as hereinbelow described) were added. Each of inner cavities 10, 10' — 90, 90' and A, A' —E, E' were loaded with antibody reagent (hereinbelow described). Disc 110, loaded as above described was rapidly accelerated in the apparatus of FIG. 1 to a first speed such that the contents of inner cavities 10, 10' — 90, 90' and A, A' —E, E' were transferred, within about 3 seconds, due to centrifugal force, to the respective communicating outer cavities 1, 1' — 9, 9' and *a, a'* — *e, e'* wherein reaction commenced and proceeded for 30 minutes.

$$T_4 + AB \rightleftharpoons AB \cdot T_4$$

$$T_4^R + AB \rightleftharpoons AB \cdot T_4^R$$

After the elapse of thirty minutes the rotational speed of the disc 110 was rapidly accelerated to a second speed and the centrifugal force developed caused the contents of cavities 1, 1' — 9, 9' and *a, a'* — E, E' to be transferred to respective communicating chromatographic columns 200. 15 seconds after acceleration of disc 110 to this second speed the eluent pump shown at 220 in FIG. 1 was activated by way of a conventional timer arrangement 212 to dispense 2 milliliters of buffer solution (hereinbelow described) from container 222 into each of the inner cavities 130 by way of dispenser 240. A total flow of 60 ml is provided by dispensing 30 ml per minute for 2 minutes, the total flow being "chopped" by the thirty cavities into 2 ml per cavity. The solution thus added by way of dispenser 240 is caused by centrifugal force to be transferred from cavities 10, 10' — 90, 90' and A, A'— E, E' to 1, 1' — 9, 9' and *a, a'* —*e, e'* to the respective chromatographic columns 200 wherein the reactants and reaction products are subject to elution due to the rotationally developed centrifugal force acting upon the eluent, and as a result T-4 antibody complex (containing both radioactive and non-radioactive T-4) together with unreacted antibody are rapidly* eluted from the individual chromatographic columns 200 and, caused by centrifugal force, to be thrown to tubes 65 as indicated at 152 in FIGS. 1 and 2. Unreacted T-4$^{-125}$I solution and serum components of low molecular weight remain in the chromatographic columns 200. In the present example, upon separation of antibody by elution, the above noted reaction is essentially halted at the time of separation in each of the chromatographic columns 200. At any convenient time after elution, tubes 65 are transferred to an arrangement of the type shown in FIG. 3 and each tube 65, with its contents 152 counted for one minute as shown in the Table below.

* e.g. within 1 minute.

TABLE

| Tube Corresding | to Location | Counts/Minute | μgm%$T_4$ | |
|---|---|---|---|---|
| a | 0 | 7623 | 0 | "Standard" levels plotted in FIG. 4 |
| a' | 0' | 7468 | 0 | |
| b | 1 | 5398 | 2 | |
| b' | 1' | 5496 | 2 | |
| c | 2 | 3194 | 6 | |
| c' | 2' | 3307 | 6 | |
| d | 3 | 2235 | 12 | |
| a' | 3' | 2325 | 12 | |
| e | 4 | 1299 | 30 | |
| e' | 4' | 1336 | 30 | |
| 1 | 5 | 4544 | 4.7 | Unknown Clinical Sample Levels determined from plot of FIG. 4 |
| 1' | 5' | 4408 | 5.1 | |
| 2 | 6 | 3009 | 8.9 | |
| 2' | 6' | 2956 | 9.0 | |
| 3 | 7 | 3919 | 6.4 | |
| 3' | 7' | 4051 | 6.1 | |
| 4 | 8 | 4092 | 6.0 | |
| 4' | 8' | 3899 | 6.4 | |
| 5 | 9 | 3415 | 7.7 | |
| 5' | 9' | 3627 | 7.1 | |
| 6 | 10 | 4500 | 4.8 | |
| 6' | 10' | 4389 | 5.2 | |
| 7 | 11 | 4092 | 6.0 | |
| 7' | 11' | 3899 | 6.4 | |
| 8 | 12 | 3225 | 8.4 | |
| 8' | 12' | 3192 | 8.2 | |
| 9 | 13 | 3501 | 7.4 | |
| 9' | 13' | 4052 | 6.0 | |

The known T-4 levels in μ gm of T-4 per 100 ml of sample of the standards *a, a'* —*e, e'*, were plotted vs the obtained counts per minute to provide the plot of FIG. 4 using the samples. The determined levels in the Table for clinical samples were obtained from the plot of FIG. 4. The following is a detailed description of the materials and procedure of the example described above.

I. Substance under Analysis

Clinical Serum Samples.

II. Materials Used

1. Thyroxine (T-4 stock), free acid: Cat. No. 2376 Sigma Chemical Co., St. Louis, Mo.
2. Thyroxine-$^{125}$I (T-4-$^{125}$): Cat. No. 6751 "Tetramet-125," Abbott Labs, North Chicago, Ill.

3. Anti-thyroxine serum (rabbit): Wien Labs., Succasunna, N.J.
4. Hydrochloric Acid: Cat. No. A-144, Fisher Scientific, New York, N.Y.
5. Sodium Hydroxide, 0.1N: Cat. No. SO-S-276, Fisher Scientific.
6. Sodium Barbital: Cat. No. B-22, Fisher Scientific.
7. Sodium Azide: Cat. No. S-227, Fisher Scientific.
8. Normal rabbit serum.
9. 8-Anilino-1-naphthalene sulfonic acid, sodium salt (ANS): Cat. No. 9041, K&K Labs, Plainview, N.Y.
10. Normal pooled human plasma: Plasma Products.
11. Activated charcoal: Darco G-60, Matheson, Coleman & Bell, Rutherford, N.J.
12. Sephadex G-25, fine (chromatographic gel): Pharmacia Fine Chemicals, Piscataway, N.J.
13. Columns (for chromatographic gel): Cat. No. 102/2, Walter Sarstedt, Inc., Princetone, N.J.
14. Tubes: 12 × 75 mm and 17 × 100 test tubes.

III. Reagents Used

A. 6N Hydrochloric Acid, 1 liter.

B. Barbital Buffer, 0.075M, pH 8.6; 1 liter. Dissolve 15.54 gm sodium barbital and 100 mg sodium azide in 800 ml distilled water. Using a standardized pH meter, bring the pH of the solution to 8.6 by the dropwise addition of 6N HCl, mixing the barbital thoroughly throughout. (Approximately 2 ml of 6N HCl is needed.) Fill up to 1 liter with distilled water. This buffer is good for one month with refrigeration.

C. 2% Normal Rabbit Serum-Barbital Buffer, 100 ml.
Add 2 ml of Normal Rabbit Serum to 98 ml of Barbital Buffer, mix thoroughly. Good for 2 weeks with refrigeration.

D. Thyroxine-free Human Plasma, 20 ml.
Thoroughly mix 3 gm of activated charcoal into 20 ml of pooled human plasma in a disposable 50 ml conical centrifuge tube, taking care to wet all the charcoal. Cover the mixture and place in regrigerator overnight. On the next day, centrifuge the mixture at about 8,000 rpm for 10 minutes. Then, using a 20 ml syringe fitted with a 25 mm Millipore filter holder with a Swinnex adaptor, filter the supernatant successively with (1) filter paper, (2) a 0.45 micron filter, (3) a 0.22 micron filter. Prepare weekly and refrigerate, or, if frozen, good for at least 3 months.

E. Thyroxine (T-4) Standards Preparation

1. T-4 Stock (0.6 mg/ml).
Dissolve 6.00 mg of T-4 Stock in a minimum volume of 0.1 N sodium hydroxide. Fill to 10 ml with distilled water. This may be aliquoted into 0.2 ml vials and stored frozed for 3 months.

2. "Working" Standards
Prepare 12 × 75 mm test tubes and label 1–5.
Prepare the T-4 Working Standards according to the following scheme:

| Tube No. | Add Barbital Buffer | Remove Buffer | Add T-4 Stock | Final Conc. |
|---|---|---|---|---|
| 1 | 1.0 ml | 0 μl | 0μl | 0 μg/ml |
| 2 | 1.0 ml | 10 μl | 10 μl T-4 Stock diluted in 3 | 2 μg/ml |
| 3 | 1.0 ml | 10 μl | 10 μl | 6 μg/ml |
| 4 | 1.0 ml | 20 μl | 20 μl | 12 μg/ml |
| 5 | 1.0 ml | 50 μl | 50 μl | 30 μl/ml . |

3. Actual Standards Used.

Label 5 17 × 100 mm test tubes 1–5; add 5.0 ml of T-4 Free Plasma to each. Remove 50 microliters of the corresponding Working Standard shown above. Mix well. The final results will be:

| Tube No. | | T-4 ng/ml | T-4 ng/35 μl | T-4 μgm/100ml |
|---|---|---|---|---|
| 1 | a | 0 | 0 | 0 |
| 2 | b | 20 | 0.7 | 2 |
| 3 | c | 60 | 2.1 | 6 |
| 4 | d | 120 | 4.2 | 12 |
| 5 | e | 300 | 10.5 | 30 |

Freeze in 0.5 ml aliquots.

F. Thyroxine $I^{125}$ Solution

1. ANS Solution
Dissolve 60 mg of 8-anilino-11-naphthanlene sulfonic acid in 10 ml of Reagent C.

2. Isotope Solution
A minimum order of Tetramet-125 is 500 microcuries. The solution is good for 6 weeks. The expiration date is given the Abbott label. The activity, i.e., the microcuries per milliliter, will vary from lot to lot; this is also given for each lot on the label. 14,000 counts per minute (CPM) is to be added to each assay tube in 50 microliters; 14,000 cpm is approximately 0.014 microcuries. Determine the total number of assay tubes, standards and unknowns, increase by 10% as a safety factor and multiply the final number by 0.014; this is the total number of microcuries needed. Next, multiply the total number of tubes, including the extra 10%, by 50. This is number of milliliters of ANS needed. Withdraw the number of microliters of Tetramet-125 corresponding to the number of microcuries and add to the correct volume of ANS. Prepare on day of use.

G. Antibody Reagent
The antibody comes from Wien Labs lyophilized in vials labeled "100 Test". Each vial is reconstituted with 14.0 ml of Reagent C. Good for 2 weeks, with refrigeration.

IV. Protocol

A. Reaction Conditions:
50 microliters T-4-$^{125}$I solution
35 microliters Standard or Serum Sample, and
65 microliters distilled water flush are mixed together.
200 microliters Antibody Reagent are added next.
The reaction is permitted to run for 30 minutes at room temperature at the first speed of the incubator/separator and when the speed is increased to the second level, the total reaction volume is transferred to a column of Sephadex G-25, fine.

The complex is eluted with 2.0 ml of Barbital Buffer. The complex is counted for 1 minute in a gamma counter.

Each sample and standard is run in duplicate Standards 1-5 occupy 10 positions.

B. Treatment of data:

The Standards are plotted as follows: counts per minute on the y-axis vs the log of $\mu$gm/100 ml on the $x$-axis. The standards as prepared above are: 0, 2, 6, 12, 30 $\mu$gm thyroxine per 100 ml. Unknowns are determined from the standard curve by finding the $\mu$gm thyroxine per 100 ml value corresponding to the unknown sample's counts.

V. Substance under Analysis

Clinical Serum Samples.

In the embodiment of the present invention illustrated by the foregoing specific example, particular advantages are obtained by essentially halting the described complex forming reaction upon rapid separation of the reaction media constituents under controlled conditions in the chromatographic columns 200. To consider a general case where reactants designated A and B are placed in inner and outer cavities 130 and 140, respectively, and caused to mix and proceed to react in the outer cavities to produce increasing amounts of a reaction product C, by separating the mixture of A, B and C on the chromatographic columns 200, into phases, one of which is collected in tubes 65 and contains at least one reactant, e.g. either A or B, the C producing reaction is essentially halted in the collecting chromatograph columns, and, even though rotation continues, no further amount of C will be produced, and hence eluted, and the parameter of the eluted phase which is to be measured, e.g. radioactivity, color, fluorescence, enzyme label, is "fixed" at essentially the same time for all of the samples being analyzed. This embodiment is of particular advantage in such applications as kinetic assays involving the determination in a sample of thyroid hormones, sex hormones, cardiac glycosides, vitamins, cancer antigens using standard radioimmunoassay reagents.

The foregoing will be more fully understood with reference to FIG. 5($a$) which schematically represents a point in time at which the unreacted portion of reactants A and B, and reaction product C have been transferred to chromatograph gel 200', but before transfer of eluent to chromatograph gel 200'. Under such conditions A and B can continue to react and produce additional amounts of C. However, upon transfer of eluent to chromatograph gel 200', which is selected in this instance to separate reactant B together with reaction product C, B and C, are rapidly separated from A into a phase which is moved along chromatograph gel 200' as indicated in FIG. 5($b$), thus halting the formation of additional reaction product C. The phase 152 comprising fixed proportions of B and C is transferred by centrifugal force to tube 65' as indicated in FIG. 5($c$) and the fixed value of the parameter of interest of either B or C can be measured in due course.

In other applications involving the process of the present invention where it is not of critical importance to halt the reaction in the chromatograph gel 200, with all samples and standards being subjected to essentially the same reaction and separation conditions, the chromatograph gel can be selected so as to elute and separate the reaction product from the reactants, particularly in the instances where any further formation of reaction product in the gel, and elution thereof will be compensated when using a simultaneously processed standard.

In the practice of the present invention the parameter of interest can be radioactivity, as particularly described hereinabove, color, fluorescence or any other suitable physical or chemical property. Accordingly, instead of a radioactive counter arrangement other conventional sensing devices known to the art can also be utilized.

In a further embodiment of the present invention, with reference to FIG. 6, a disc 510, is employed having a plurality of single cavities 520 instead of a pair of radially aligned cavities 130 and 140, as in the device of FIG. 1. In the practice of the invention using the apparatus of FIG. 6, precise amounts of two or more reactants, e.g., serum and reagent indicated at 525 are placed in cavities 520 wherein a reaction occurs to provide a physically separatable reaction product. Loading of the cavities 520 can be accomplished by pipetting as previously disclosed. One or more of cavities 520 can be loaded with standard reactants in the manner previously described and the thus loaded disc 510 can be positioned on support member 15 in the same manner as disc 110 in FIG. 1, and rotated at a speed sufficient to cause the contents of the cavities 520 to be transferred by centrifugal force into communicating separating media 190. From this point on the process proceeds in the same manner as previously described in connection with the apparatus arrangement of FIG. 1 and a standard as exemplified in in FIG. 4. In practicing the foregoing embodiment as disc 510 containing cavities 520 can be loaded with reactants and the reaction permitted to go to equilibrium. That is to say, the discs 510 can be loaded and stored for extended periods of time, e.g. for hours or more after which the discs 510 can be arranged in place of discs 110 in the devices of FIG. 1 and an assay performed as previously described. This embodiment can be effectively employed with slow reactions, e.g. the determination in blood serum of human growth hormone, which if using the previously described dual cavity embodiment would entail impractically long rotation at the higher speeds, e.g. 1 hour or more. Alternatively, where the discs 510 are loaded in a period of time such that for the particular slow reaction involved, it can be considered as a practical matter that the reactions in the different single cavities have all started at the same time, the loaded disc 510 can be rotated and the contents of the cavities 520 transferred to communicating separating media 190 at any time that a measurable amount of separatable constituent has been produced in cavities 520. This procedure is effective in instances where any loss of assay accuracy which might result from the different reaction times in the various cavities is not significant as compared with the time saved.

Particular advantages of the mechanically and chemically continuous tandem method of the present invention include the essential elimination of manual or mechanical intervention in the course of performing an assay which minimizes the significance of variables other than those of interest, and the ability to utilize short reaction times and permit simultaneous kinetic studies under controlled time conditions.

For purposes of the present invention reactive constituents include substances which will react chemically to provide a chemically different reaction product or products and also substances which can be considered to react physically (e.g. certain physical adsorption phenomena) to produce one or more physical different materials.

The liquid phase separating medium in the practice of the present invention can be conventional chromatographic arrangements, for example, which provide separation on the basis of molecular size, physical adsorption phenomena, chemisorption, ion exchange properties, specific molecular affinities (affinity chromatography) and other known techniques utilizing for example, gels, solids, and resins.

What is claimed is:

1. A method for assaying a plurality of liquid samples which comprises i. reacting at least two liquid materials in a plurality of cavities to provide a liquid containing at least one reaction product ii. providing liquid phase separating means in communication with said cavities iii. subjecting said cavities and said liquid phase separating means to centrifugal force sufficient to transfer the liquid contents of said cavities to said communicating liquid phase separating means and provide separation of the liquid transferred thereto into at least two phases, and iv. measuring at least one property of a separated phase.

2. A method in accordance with claim 1, wherein at least one of said liquid materials contains a radioactive constituent and the property measured in step (iv) is radioactivity.

3. A method in accordance with claim 1 wherein transfer of the contents of said cavities to said liquid phase separating means occurs at a time when increasing amounts of at least one reaction product at being formed.

4. A method in accordance with claim 1 wherein at least one of said phases separated in said liquid phase separating means is transferred from said liquid phase separating means by centrifugal force developed by rotation of said rotatable means.

5. A method in accordance with claim 1 wherein at least one of said phases separated in said liquid phase separating means is transferred from said liquid phase separating means to a vessel in communication therewith by centrifugal force.

6. A method in accordance with claim 1 wherein said phase transferred to said vessel is radioactive.

7. A method in accordance with claim 1 wherein at least one property of said phase transferred to said vessel is measured.

8. A method in accordance with claim 1 wherein a liquid is introduced into said cavities subsequent to the transfer of liquid to said liquid phase separating means and during rotation thereof to provide an eluent in said liquid phase separating means upon transfer thereto by centrifugal force.

9. A method in accordance with claim 1 wherein at least one of said cavities contains liquid materials which provide upon reaction a definitive value of measurable property in at least one of said separated phases.

10. A method for assaying a plurality of liquid samples which comprises i. providing liquid material in a plurality of substantially circularly disposed first cavities ii. providing a different liquid material, reactable with said material in said first cavities, in a plurality of substantially circularly disposed second cavities iii. providing a plurality of liquid phase separating means in a substantially circular arrangement, said first and second cavities and said liquid phase separating means being arranged substantially concentric about a common axis with said liquid phase separating means being at a further radial distance than said second cavities and said second cavities being at a further radial distance than said first cavities, said liquid phase separating means being in tandem communication with a second cavity which is in tandem communication with a first cavity;

iv. causing rotation of said cavities about said common axis to develop a centrifugal force sufficient to cause liquid in said first cavities to be transferred to said second cavities to react with said liquid in said second cavities to produce at least one reaction product v. subsequently causing rotation of said cavities and said liquid phase separating means at a speed to develop a centrifugal force sufficient to transfer the liquid contents of said second cavities to said liquid phase separating means vi. continuing rotation of said liquid phase separating means to develop a centrifugal force sufficient to separate the liquid transferred thereto into at least two phases and vii. measuring at least one property of at least one of said phases.

11. A method in accordance with claim 10 wherein at least one of said liquid material contains a radioactive constituent and the property measured in step (vii) is radioactivity.

12. A method in accordance with claim 10 wherein transfer of the contents of said second cavities to said liquid phase separating means occurs at a time when increasing amounts of at least one reaction product are being formed.

13. A method in accordance with claim 10 wherein at least one of said phases separated in said liquid phase separating means is transferred from said liquid phase separating means by centrifugal force developed by rotation of said rotatable means.

14. A method in accordance with claim 10 wherein at least one of said phases separated in said liquid phase separating means is transferred from said liquid phase separating means to a vessel in communication therewith by centrifugal force.

15. A method in accordance with claim 10 wherein a liquid is introduced into at least said second cavities subsequent to the transfer of liquid to said liquid phase separating means and during rotation thereof to provide an eluent in said liquid phase separating means upon transfer thereto by centrifugal force.

16. A method in accordance with claim 10 wherein at least one of said first cavities and one of said second cavities contain liquid materials which provide upon reaction a definitive value of a measurable property in at least one of said separated phases.

17. A method for assaying a plurality of liquid samples which comprises i. providing rotatable means having rotatable therewith a plurality of first and second cavities each of said cavities being adapted to contain liquid and said cavities being arranged in communication with each other such that upon development of a sufficient centrifugal force by rotation of said rotatable means, liquid in a said first cavity is transferred to said second cavity, and upon development of a sufficient centrifugal force by rotation of said rotatable means liquid in a said second cavity is transferred out of said second cavity ii. providing at least one liquid material in a plurality of said first cavities and at least one different liquid material in a plurality of said second cavities said materials being such that upon contact therebetween interaction occurs to provide in said second cavities a mixture having at least one separatable constituent capable of being separated from said mixture by liquid phase separating means iii. causing rotation of said rotatable member to develop a centrifugal force sufficient to transfer the liquid contents of said first cavities to the second cavities to contact the liquid contents of the second cavities to provide a mixture confined in said second cavity containing at least one separatable constituent capable of being separated from said mixture by liquid phase separating means iv. providing liquid phase separating means in communication with said second cavities and arranged to be rotatable therewith and be subjected to centrifugal force developed by rotation of said rotatable means v. adjusting the speed of the rotatable means at a time subsequent to the formation of said separatable constituent in said second cavities to the extent that there is provided a centrifugal force sufficient to transfer the mixture in said second cavities to said liquid phase separating means, vi. continuing rotation of said rotatable means to provide a centrifugal force acting upon the mixture transferred to said liquid phase separating means sufficient to cause said mixture to be separated into at least two phases, one of said phases containing at least one of said separatable constituent of said mixture and vii. measuring at least one property of a said phase containing said at least one separatable constituent.

18. A method in accordance with claim 17 wherein i. said at least one liquid material provided in said first cavity contains at least one reactive constituent;

ii. said at least one liquid material provided in said second cavity contains at least one reactive constituent, iii. said reactive constituents, upon transfer of the liquid contents of said first cavity to said second cavity, proceed to react in said second cavity with the formation of a reaction product iv. one of said at least two phases separated in said liquid phase separating means contains substantially all of at least one, but not all of said reactive constituents in said mixture transferred to said liquid phase separating means.

19. A method in accordance with claim 17 wherein at least one of said liquids contains a radioactive constituent and the property measured in step (vii) is radioactivity.

20. A method in accordance with claim 18 wherein at least one of said reactable constituents is radioactive.

21. A method in accordance with claim 18 wherein transfer of the contents of the second cavity to said liquid phase separating means occurs at a time when the reactive constituents are reacting with the formation of increasing amounts of reaction product.

22. A method in accordance with claim 17 wherein at least one of said phases separated in said liquid phase separating means is transferred from said liquid phase separating means by centrifugal force developed by rotation of said rotatable means.

23. A method in accordance with claim 17 wherein at least one of said phases separated in said liquid phase separating means is transferred from said liquid phase separating means to a vessel in communication therewith by centrifugal force developed by rotation of said rotatable means.

24. A method in accordance with claim 23 wherein said phase transferred to said vessel is radioactive.

25. A method in accordance with claim 23 wherein at least one property of said phase transferred to said vessel is measured.

26. A method in accordance with claim 17 hwerein at least one of said first cavities and one oof said second cavities contain liquid materials which provide upon reaction a definitive value of a measurable property in at least one of said separated phases.

27. A method in accordance with claim 17 wherein a liquid is introduced into at least said second cavities subsequent to the transfer of liquid to said liquid phase separating means and during rotation thereof to provide an eluent in said liquid phase separating means upon transfer thereto by centrifugal force.

28. Assay apparatus comprising a i. rotatable member having a plurality of substantially circularly disposed first cavities adapted to contain liquid and a plurality of substantially circularly disposed second cavities adapted to contain liquid ii. a plurality of liquid phase separating means arranged in a substantially circular arrangement and engaged to said rotatable member, said first and second cavities and said liquid phase separating means being arranged substantially concentric about a common axis with said liquid phase separating means being at a further radial distance than said second cavities and said second cavities being at a further radial distance that said first cavities, said liquid phase separating means being in tandem communication with a second cavity which is in tandem communication with a first cavity and (iii) collecting means adapted to contain liquid engaged to said liquid phase separating means to receive liquid separated by said liquid phase separating means.

29. Assay apparatus comprising i. rotating means ii. a disc shaped member adapted to be rotated in a substantially horizontal plane about its central axis by said rotating means, said disc member having a first row of a plurality of cavities adapted to contain liquid at a common radial distance from the central axis of said disc and a second row of a plurality of cavities adapted to contain liquid at a different and greater common radial distance from said first row, cavities of said first row being in substantial radial aligment with cavities of said second row;

iii. first trough-like means having an upward slope between aligned cavities of said first row and said second row to provide communication therebetween for liquid over flowing from a cavity of said first row to a radially aligned cavity of said second row due to centrifugal force;

iv. a plurality of liquid phase separating means substantially in radial alignment with cavities of said second row and adapted to be rotated by said rotating means;

v. second trough-like means having an upward slope between the aligned cavities of said second row and said liquid phase separating means to provide communication therebetween for liquid overflowing from a cavity of said second row due to centrifugal force, said second trough-like means having a steeper slope than said first trough like means such that a centrifugal force required to cause overflow of liquid from the cavities of the second row is greater than the centrifugal force required to cause overflow of liquid from the cavities of the first row.

30. Apparatus in accordance with claim 29 wherein said plurality of liquid phase separating means are in the form of individual pivotally mounted columns adapted to be displaced by centrifugal force to positions wherein the longitudinal axis of said columns extend substantially radially with respect to the central axis of said disc shaped member.

31. Apparatus for use with a centrifugal assay device comprising i. a disc shaped member adapted to be rotated in a substantially horizontal plane about its central axis, said disc shaped member having a first row of a plurality of cavities adapted to contain liquid at a common radial distance from the central axis of said disc and a second row of a plurality of cavities adapted to contain liquid at a different and greater common radial distance from said first row, cavities of said first row being in substantial radial alignment with cavities of said second row;

ii. first trough-like means having an upward slope between aligned cavities of said first row and said second row to provide communication therebetween for liquid over flowing from a cavity of said first row to a radially aligned cavity of said second row due to centrigugal force;

iii. second trough-like means having an upward slope at the radially outermost portion of the aligned cavities of said second row to provide exit therefrom for liquid overflowing from a cavity of said second row due to centrifugal force, said second trough-like means having a steeper slope than said first trough-like means such that a centrifugal force required to cause overflow of liquid from the cavities of the second row is greater than the centrifugal force required to cause overflow of liquid from the cavities of the first row.

* * * * *